United States Patent [19]
Lerman et al.

[11] Patent Number: 5,632,724
[45] Date of Patent: May 27, 1997

[54] HYPEREXTENSION THORACO-LUMBAR BRACE

[75] Inventors: Max Lerman, Beverly Hills; Vick G. Bonessa, Arcadia, both of Calif.

[73] Assignee: United States Manufacturing Company, Pasadena, Calif.

[21] Appl. No.: 598,471

[22] Filed: Feb. 8, 1996

[51] Int. Cl.$^6$ .................................................. A61F 5/01
[52] U.S. Cl. ........................... 602/19; 128/845; 606/237
[58] Field of Search ................................ 128/845; 602/5, 602/19; 606/237, 240–241, 245

[56] References Cited

U.S. PATENT DOCUMENTS

| | | | |
|---|---|---|---|
| Re. 31,564 | 4/1984 | Hendricks | 602/19 |
| 2,582,930 | 1/1952 | Jewett . | |
| 2,808,050 | 10/1957 | Ward . | |
| 4,173,973 | 11/1979 | Hendricks . | |
| 4,628,913 | 12/1986 | Lerman | 602/19 X |
| 4,640,269 | 2/1987 | Goins | 602/19 |
| 4,976,257 | 12/1990 | Akin et al. | 602/19 |
| 5,135,471 | 8/1992 | Houswerth | 602/19 |
| 5,342,289 | 8/1994 | Munny | 602/19 |

FOREIGN PATENT DOCUMENTS 1197192  7/1965  Germany ......................... 602/19

*Primary Examiner*—Richard J. Apley
*Assistant Examiner*—David R. Risley
*Attorney, Agent, or Firm*—Christie, Parker & Hale, LLP

[57] ABSTRACT

A hyperextension brace includes an upright support frame and a sternum pad positioned at one end of the upright support frame and a pubic pad positioned at the opposite end of the upright support frame. The brace further includes self-adjusting connectors for pivotally attaching the pads to the ends of the vertical support frame. The self-adjusting connectors comprise a one-piece structure having a generally flat web section integrally molded with an elongated, narrow recessed portion projecting from and reinforcing the web section. The recessed portion has an open end opening into an internal cavity for slidably receiving the end portions of the upright support frame. The one-piece connector further includes a U-shaped flange section integrally molded with and extending away from an end of the recessed portion opposite from its open end. The flange section has an elongated mounting surface generally parallel to and to the rear of the web section and bendable toward and away from the web section and its recessed portion. The self-adjusting connectors provide an infinite number of flexible axes for the sternum and pubic pads to rotate about with respect to the upright support frame, thereby conforming to anatomical differences in the human body.

19 Claims, 3 Drawing Sheets

HYPEREXTENSION THORACO-LUMBAR BRACE

FIELD OF THE INVENTION

This invention relates generally to medical devices, and more particularly to a hyperextension thoraco-lumbar brace, including a frame assembly, sternum and pubic pads, and self-adjusting connectors for attaching the sternum and pubic pads to the frame assembly and providing multiple axis flexibility for the pads.

BACKGROUND OF THE INVENTION

Hyperextension braces are known to provide relief to patients suffering from diseases such as osteoporosis or from spinal injuries. The principal purposes of such braces are to hyperextend the spine to provide relief of pain and allow individual vertebrae to heal. A hyperextension brace is applied to the torso of the human body, applying pressure to the sternum and pubic area in connection with a lumbar pad and straps for tensioning the brace, causing hyperextension of the spine.

A problem with early hyperextension back braces is that the sternum and pubic pads were attached to the frame by a rigid mechanical hinge. Considering the frame and the hinge were relatively stiff, there was little to no flexibility of the pads in relation to the body of the patient. Consequently, initially hyperextension back braces were uncomfortable for the patient and could not be adjusted to accommodate individual patient sizes.

A hyperextension back brace, as disclosed in U.S. Pat. No. 4,173,973 to Hendrix, recognized the problem of inflexibility between the sternum and pubic pads and the brace frame. Hendrix attempted to address this problem by incorporating a plastic attachment element bonded between the pad and the brace frame to provide a "living hinge." The attachment element is disclosed as being capable of flexing about a plurality of axes to bend and twist and thus enable the sternum pad to readily conform to variations in sternum shapes and forms.

A problem with the Hendrix brace is that its plastic attachment element is a thin strip bonded to a single surface of the metal brace frame. A problem with this design is that the plastic attachment element, being only a thin strip of plastic, would fail or be easily broken loose from its connection with the brace frame. Consequently, the Hendrix brace would constantly be in need of repair and be unavailable for the user. The hyperextension brace of this invention is based on the recognition of the problems associated with the plastic attachment mechanism and has solved these problems by eliminating the plastic attachment mechanism and utilizing a rigid mechanical hinge.

Thus, there exists a long-felt need in the art for a new and improved hyperextension brace which provides flexibility between the working ends of the pads and the frame, is light weight, inexpensive to manufacture, and has long term reliability.

SUMMARY OF THE INVENTION

The present invention provides an improved hyperextension brace which eliminates the problems of prior existing braces and is simple and inexpensive to manufacture.

In one embodiment of the invention, the hyperextension brace comprises an upright brace frame, a sternum pad and a pubic pad located at opposite ends of the upright brace frame, and a self-adjusting connector positioned between the sternum pad and one end of the upright brace frame and a second self-adjusting connector positioned between the pubic pad and the opposite end of the upright brace frame.

The self-adjusting connector is a one-piece molded plastic support which includes a recessed region in which the end of the upright brace frame is removably inserted. The self-adjusting connector also includes a generally U-shaped bendable flange which extends outwardly opposite from the recessed region to provide a mounting surface for fixed attachment of the sternum and pubic pads. The sternum and pubic pads are elongated semi-rigid supports which in combination with the flange provide multiple bending axes enabling the sternum and pubic pads to readily conform to variations in the torso of various users. Each recess provides structural integrity for the attachment of the connector to the upright brace frame.

The hyperextension brace of the present invention further includes a horizontal brace frame intersecting with and attached to the mid point of the upright brace frame. A lumbar pad is provided for positioning around the lower back of the user and is attached to the horizontal brace frame member by a flexible strap. The strap can be configured such that the brace can be adjusted by the user in front of or behind their torso.

These and other aspects of the invention will be more fully described in the following detailed description and the accompanying drawings.

DETAILED DESCRIPTION

Figure 1:
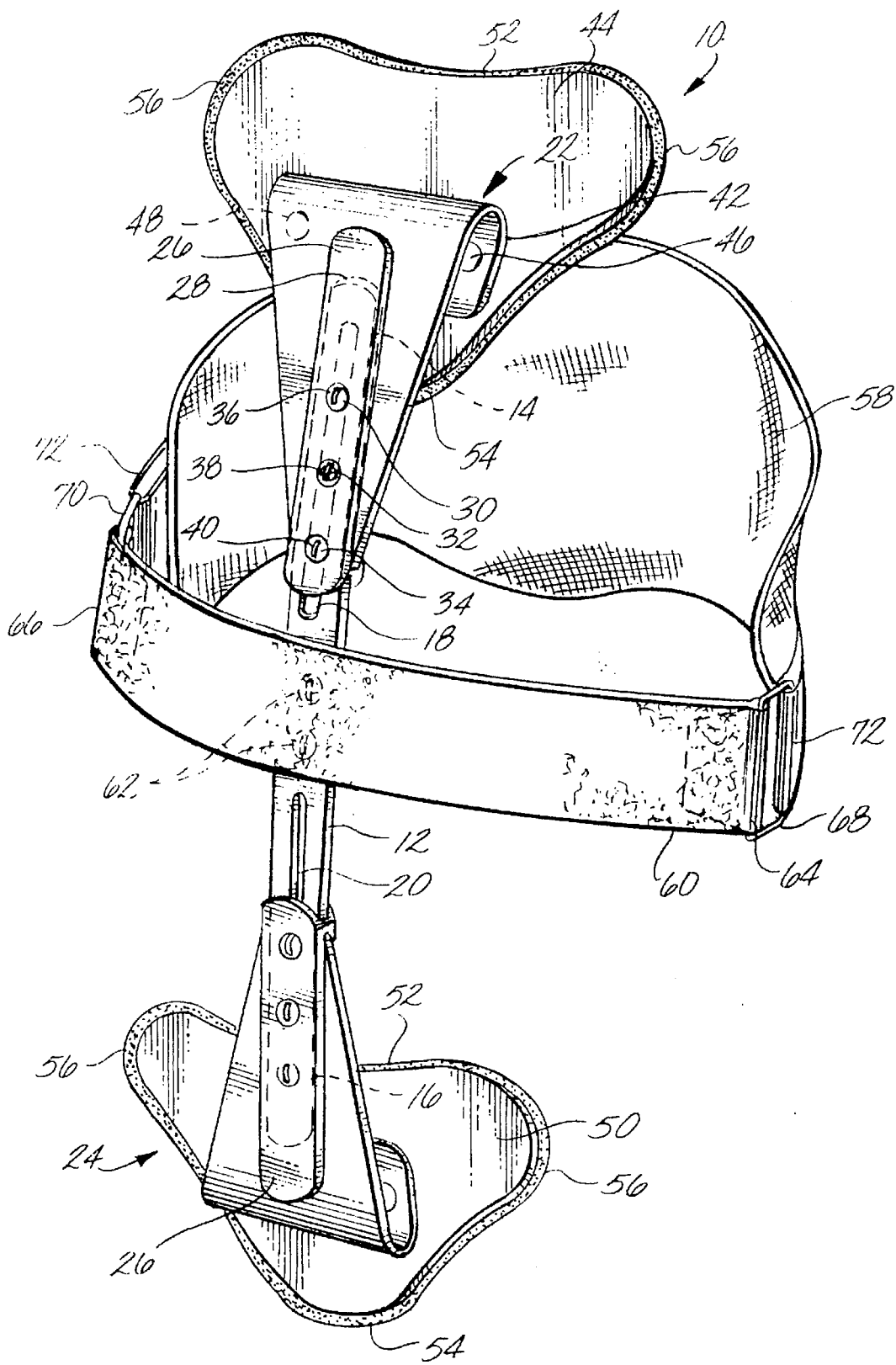
FIG. 1 is a perspective view showing one embodiment of a hyperextension brace of the present invention.
Figure 2:
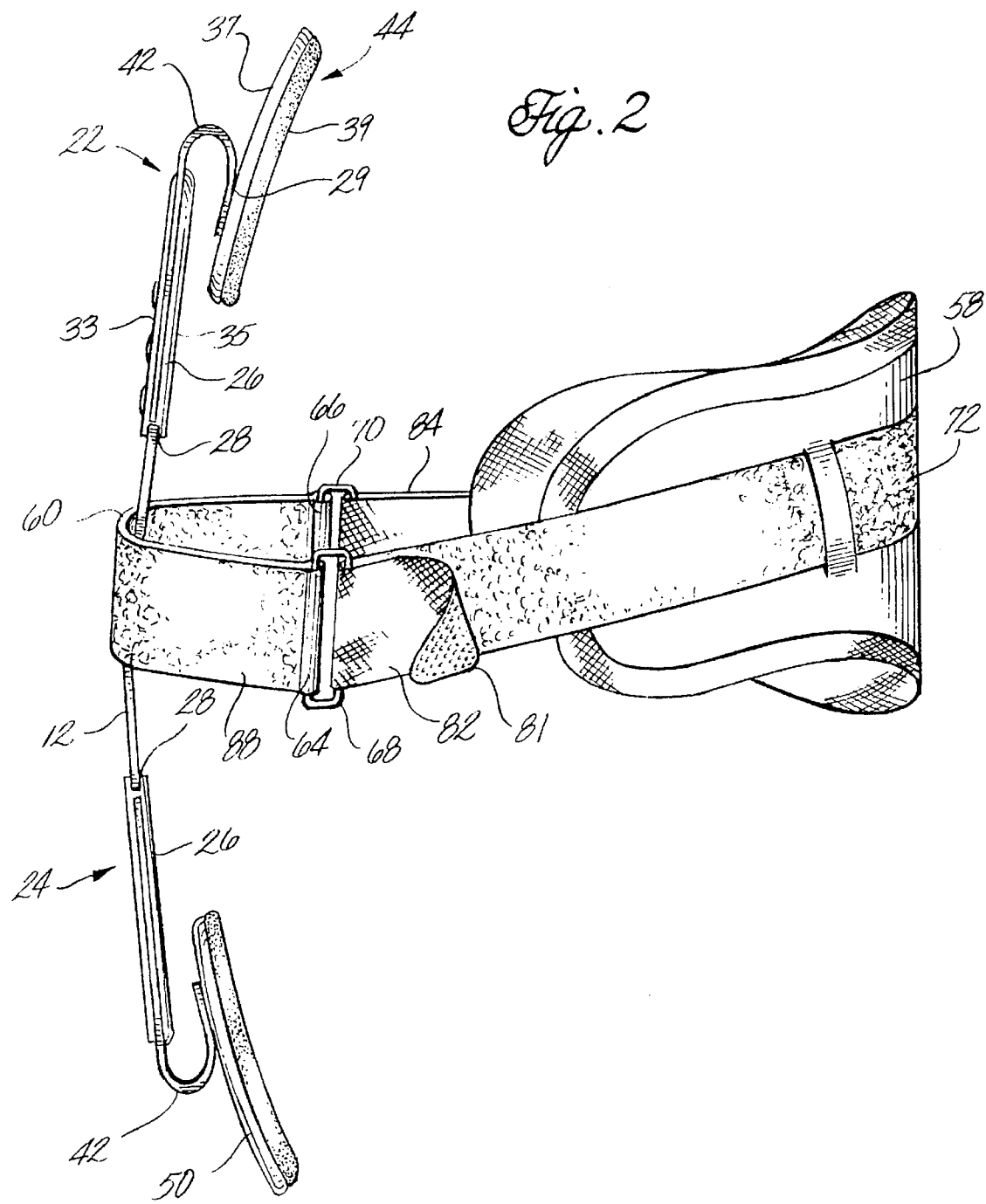
FIG. 2 is a side view of the brace of FIG. 1.

Referring to the drawings, FIGS. 1 and 2 illustrate a hyperextension brace 10 which includes a vertical or upright support frame 12 having an upper end 14 and a lower end 16. Ends 14 and 16 each include a corresponding vertical slot 18, 20, respectively, and are bent slightly inwardly. Vertical support frame 12 is preferably made from a one-quarter gauge 2041 aluminum alloy. Support frame 12 is shaped so as to be concave toward the body of a user.

Separate self-adjusting connectors 22 and 24 are located at the upper and lower ends of the vertical support frame, respectively. Connectors 22 and 24 are structurally similar and consequently the following detailed description will be limited to connector 22. Connector 22 has a female portion 26 having a downwardly opening internal recess 28 for slidably receiving the end 14 of the support frame 12. The female portion has a plurality of bores 30, 32 and 34 which receive screws 36, 38, and 40 for adjustably positioning the connector to the end of the upright support frame. The connector is adjustable by loosening the screws which pass through a narrow, elongated slot 18 and pulling or retracting the connector to the appropriate position along the slot and then tightening the screws to lock the connector in the desired position. Screws 36, 38 and 40 are tightened by nuts (one nut 41 is shown on the backside of connector 22 in FIG. 3).

Connector 22 further includes a U-shaped flange 42 extending from the female portion. Flange 42 provides a surface for attaching a sternum pad 44. Sternum pad 44 is attached to the U-shaped flange by rivets 46, 48, or by other suitable fasteners such as adhesives. The sternum pad comprises a semirigid hard plastic front face 37 with a compressible foam pad on its rear face 39 for patient contact.

More specifically, the connector 22 is a semirigid one-piece hinge made from a molded plastic material. The connector has an upwardly diverging generally inverted triangular-shaped thin, flat web section 27 for facing the front side of the brace. The top of the web section at its area of maximum width has an inverted U-shaped flange section 42 forming an elongated generally flat mounting surface 29 spaced to the rear of the front web section 27. The rear mounting surface lies flat against a front face 37 of the sternum pad 44. The long narrow upright recessed female portion 26 is of generally uniform width from end to end and extends upwardly along most of the length of the web section, generally along its central axis. As shown best in FIG. 2, the recess 28 is of generally uniform depth from end to end, and front 33 and rear 35 faces of the recess lie in front of and to the rear of and are uniformly spaced from the opposite faces of the flat web section 27. Thus, a reinforced structure is formed along the central axis of the web section by the projecting front and rear faces of the long recessed region. The connector is preferably made from a molded polymeric material such as polypropylene and provides a rigid structure for attaching the sternum pad 44 to the rear mounting face 29 of the U-shaped flange section The mounting face of the flanged section is bendable toward and away from the rigid web section of the connector and thereby provides a means of pivoting the sternum pad about an axis extending parallel to the top edge of the connector. By pivoting, the flange section allows the brace to apply stabilizing pressure to the sternum and pubic bone and to conform to each individual patient size.

The female portion and recess construction of the connector overcomes the failure problems of previous plastic connectors in that the female portion surrounds the end of the frame support 12 thereby reinforcing the support frame as well as providing structural rigidity for the connector.

The hard plastic front faces of the sternum pad 44 and pubic pad 50 are made from a plastic material such as high density polyethylene. The compressible pads on the rear faces are made of a foamed plastic material such as polyethylene or polyurethane foam. Pads 44 and 50 are identically shaped and include an upper concave edge 52, a lower convex edge 54 and rounded side edges 56 for joining the upper and lower edges. The pads are shaped to give the user the greatest possible freedom of movement in the neck area while still applying the necessary contact forces to the torso.

Hyperextension brace 10 also includes a lumbar pad 58 connected to a horizontal support frame 60. Frame 60 is also preferably an aluminum alloy which is attached to upright support frame 12 by screws 62. Frame 60 is also shaped so as to be concave toward the wearer. Located on each end of horizontal support frame 60 are clips 64 and 66 for holding rings 68 and 70. Lumbar pad 58 attaches to the horizontal support frame 60 by a flexible strap 72 which passes through rings 68 and 70.

Figure 3:
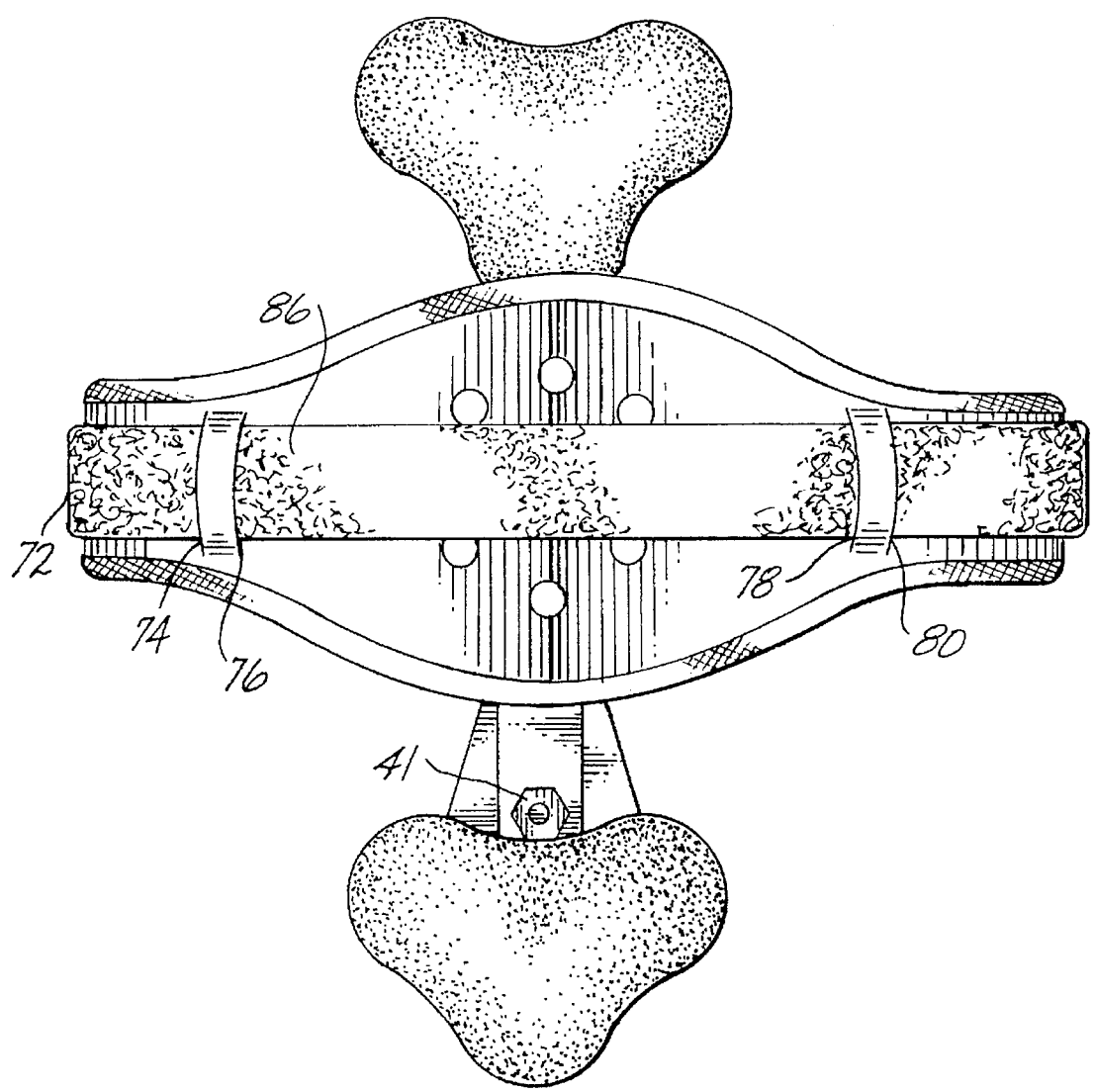
FIG. 3 is a rear view of the brace of FIG. 1.

As shown in FIG. 3, the back side of lumbar pad 58 includes slots 74, 76, 78 and 80 through which strap 72 is threaded to hold the lumbar pad in position on the wearer. Strap 72 is preferably made from nylon having hook fasteners 81 located at ends 82 and 84 (FIG. 2) with the remaining middle portion of strap 72 containing loop fasteners 86. A strip of loop fastener 88 also is positioned on the outwardly facing surface of horizontal support frame 60. The hook and loop fasteners can be the well-known fastener materials sold under the mark VELCRO.

The brace is positioned on the user by adjusting connector 22 and 24 to the appropriate position along the vertical support frame so that the sternum pad and pubic pad rest on the sternum and the pubic bone of the user. The lumbar pad is then positioned on a lower back of the wearer and the strap is threaded through rings 68 and 70 and then pulled tightly and fastened in loop fastener 86 behind the wearer.

Alternatively, the brace can be tightened on the front side of the wearer by threading strap 72 through slots 74–80 so that when ends 82 and 84 are threaded through rings 68 and 70, their hook fasteners can be attached to loop fastener 88 located on the front of the horizontal support frame. The brace of the present invention has been designed so that the strap can be secured in either the front or the back of the wearer to accommodate those patients who cannot reach behind themselves to tighten the brace.

What is claimed is:

1. A hyperextension brace comprising:

a rigid vertical support frame having an upper end and a lower end;

a sternum pad positioned on the upper end of the support frame;

a pubic pad positioned on the lower end of the support frame;

a self-adjusting connector for pivotally attaching the sternum pad to the upper end of the support frame, the self-adjusting connector comprising a one-piece structure having a generally flat web section integrally molded with and projecting away from an elongated, narrow female portion, the female portion reinforcing the web section and having an open end opening into an internal cavity for slidably receiving the upper end portion of the vertical support frame, the one-piece connector further including a U-shaped flange section integrally molded with and extending away from an end of the female portion opposite from its open end, the flange section having an elongated mounting surface spaced generally parallel to the web section and bendable toward and away from the web section and the female portion; and fastener means for maintaining the brace in position on a torso of a human body.

2. The brace of claim 1 wherein the brace further includes a second self-adjusting connector for pivotally attaching the pubic pad to the lower end of the vertical support frame.

3. The brace of claim 2 wherein the second self-adjusting connector comprises a one-piece structure having a generally flat web section integrally molded with and projecting away from an elongated, narrow female portion, the female portion reinforcing the web section and having an open end opening into an internal cavity for slidably receiving the lower end portion of the vertical support frame, the one-piece connector further including a U-shaped flange section integrally molded with and extending away from an end of the female portion opposite from its open end, the flange section having an elongated mounting surface spaced generally parallel to the web section and bendable toward and away from the web section and the female portion.

4. The brace of claim 3 wherein the upper end and the lower end of the vertical support frame include a slot for slidably engaging the self-adjusting connectors.

5. The brace of claim 4 wherein the female portion of the self-adjusting connectors include at least one bore aligned with the slots for adjustably securing the connectors to the vertical support frame.

6. The brace of claim 1 wherein the means for maintaining the brace on the torso of a wearer comprises a horizontal support frame rigidly connected to the vertical support frame, a lumbar pad, and a flexible strap for connecting the lumbar pad to the horizontal support frame.

7. The brace of claim 6 wherein the strap includes hook and loop fasteners for securing the strap behind the lumbar pad.

8. The brace of claim 6 wherein the horizontal support frame includes loop fasteners positioned on an outer surface for securing the strap in front of the wearer.

9. A medical device for hyperextending the spine of a human body comprising:

a vertical support frame having a first end and a second end;

a horizontal support frame intersecting the vertical support frame;

a sternum pad positioned at the first end;

a pubic pad positioned at the second end;

a first self-adjusting connector for attaching the sternum pad to the first end;

a second self-adjusting connector for attaching the pubic pad to the second end;

the first self-adjusting connector having a web portion and an integrally molded female portion for receiving the first end and a U-shaped portion extending away from the female portion providing a surface for attaching the sternum pad;

the second self-adjusting connector having a web portion and an integrally molded female portion for receiving the second end and a U-shaped portion extending away from the female portion providing a surface for attaching the pubic pad; and a lumbar pad connected to the horizontal support frame for securely maintaining the device on the body.

10. The medical device of claim 9 wherein the first end and second end of the vertical support frame each includes a slot for slidably engaging the first and second self-adjusting connectors.

11. The medical device of claim 10 wherein the female portions of the adjustable connectors include at least one bore aligned with the slots for adjustably securing the connectors to the vertical support frame.

12. The medical device of claim 9 wherein the lumbar pad is connected to the horizontal support frame by a strap, the strap having hook and loop fasteners for securing the strap behind the lumbar pad.

13. The medical device of claim 9 wherein the lumbar pad is connected to the horizontal support frame by a strap, the strap including hook fasteners securable to loop fasteners positioned on a front surface of the horizontal support frame.

14. A hyperextension back brace comprising:

a vertical support frame having a first end and a second end;

a sternum pad positioned at the first end;

a pubic pad positioned at the second end;

a first self-adjusting connector for attaching the sternum pad to the first end, the first self-adjusting connector having a web portion integrally molded to a female portion for receiving the first end and a U-shaped flange extending from the female portion for attaching the sternum pad;

a second self-adjusting connector for attaching the pubic pad to the second end, the second self-adjusting connector having a web portion integrally molded to a female portion for receiving the second end and a U-shaped flange extending from the female portion for attaching the sternum pad; and means for maintaining the brace in position on a torso of a human body.

15. The hyperextension back brace of claim 14 wherein the first end and the second end of the vertical support frame each includes a slot for slidably engaging the self adjusting connectors.

16. The hyperextension back brace of claim 14 wherein the female portions include at least one bore aligned with the slots for adjustably securing the connectors to the vertical support frame.

17. The hyperextension back brace of claim 14 wherein the means for maintaining the brace on the torso comprises a lumbar pad and a strap for connecting the lumbar pad to the horizontal support frame.

18. The back brace of claim 17 wherein the strap includes hook and loop fasteners for securing the strap behind the lumbar pad.

19. The back brace of claim 18 wherein the horizontal support frame includes loop fasteners positioned on a front surface for connecting hook fasteners on the strap and securing the strap in front of the torso.

* * * * *